(12) United States Patent  (10) Patent No.: US 8,101,944 B2
Li et al.  (45) Date of Patent: Jan. 24, 2012

(54) ORGANIC SEMICONDUCTOR MATERIAL AND ORGANIC TRANSISTOR USING THE SAME

(75) Inventors: Jian Li, Jiangsu (CN); Hiroyuki Fujii, Shiga (JP)

(73) Assignee: SANYO Electric Co., Ltd., Moriguchi (JP)

( * ) Notice: Subject to any disclaimer, the term of this patent is extended or adjusted under 35 U.S.C. 154(b) by 750 days.

(21) Appl. No.: 12/077,473

(22) Filed: Mar. 18, 2008

(65) Prior Publication Data

US 2008/0230776 A1    Sep. 25, 2008

(30) Foreign Application Priority Data

Mar. 20, 2007   (JP) .................. 2007-072062

(51) Int. Cl.
 *H01L 21/44* (2006.01)
(52) U.S. Cl. .................. 257/40; 257/E51.006; 438/99; 252/500
(58) Field of Classification Search .......... 257/40, 257/E51.006; 438/99; 252/500
See application file for complete search history.

(56) References Cited

U.S. PATENT DOCUMENTS

| | | | | | |
|---|---|---|---|---|---|
| 4,900,782 | A | * | 2/1990 | Han et al. ................ | 525/398 |
| 5,213,714 | A | * | 5/1993 | Kampf et al. ............ | 252/500 |
| 5,225,109 | A | * | 7/1993 | Feldhues et al. ......... | 252/500 |
| 6,518,949 | B2 | * | 2/2003 | Drzaic .................... | 345/107 |
| 7,048,874 | B2 | * | 5/2006 | Louwet et al. ........... | 252/500 |

FOREIGN PATENT DOCUMENTS

| | | |
|---|---|---|
| JP | 2006-037098 | 2/2006 |
| JP | 2006-117672 | 5/2006 |

* cited by examiner

*Primary Examiner* — Matthew Landau
*Assistant Examiner* — Colleen E Snow
(74) *Attorney, Agent, or Firm* — Masuvalley & Partners

(57) ABSTRACT

The invention relates to an organic semiconductor material with a high carrier mobility, which is capable of obtaining favorable semiconductor characteristics when used in an organic semiconductor device, and an organic transistor using the same. More specifically, the present invention has a following structure including an oligothiophene part and a connecting part G;

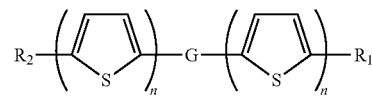

where, $R_1$ and $R_2$ are a hydrogen, a alkyl group, an alkoxy group, an aryl group, or an alkenyl group, $R_1$ and $R_2$ may be identical or different from each other, and where n is an integer. In the organic semiconductor material, the structure of the connecting part G may be any of the following:

-continued
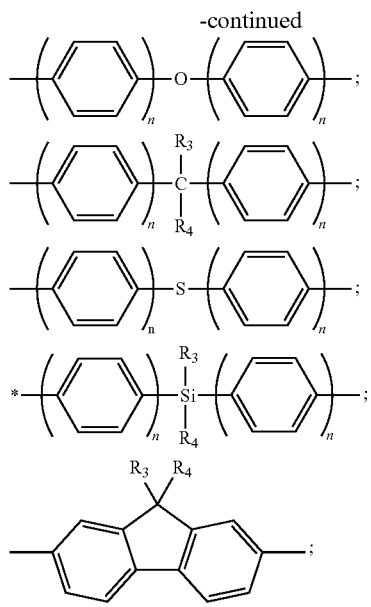
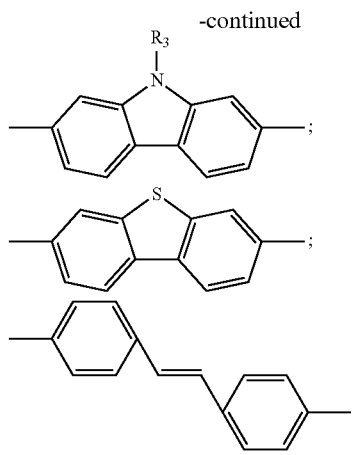
where, $R_3$ and $R_4$ are a hydrogen, an alkyl group, an alkoxy group, an aryl group, or a alkenyl group, $R_3$ and $R_4$ may be identical or different from each other, and where n is an integer of 1 to 3.
10 Claims, 15 Drawing Sheets

(Embodiment 2)

(Embodiment 3)

(Embodiment 6)

(Embodiment 8)

(Comparative Example 1)

(Embodiment 9)

(Embodiment 10)

(Embodiment 11)

ORGANIC SEMICONDUCTOR MATERIAL AND ORGANIC TRANSISTOR USING THE SAME

TECHNICAL FIELD

The present invention relates to an organic semiconductor material and an organic transistor using the same.

BACKGROUND OF THE INVENTION

In recent years, use of an organic semiconductor material has been considered for semiconductor devices, such as transistors, diodes, and thyristors, which conventionally use inorganic semiconductor materials, such as silicon and gallium arsenide. Most of the organic semiconductor materials are capable of evaporating in a relatively low temperature, such as 100 degree/C. to 200 degree/C. Also, by dissolving into a solution, a semiconductor layer may be formed by a printing method, such as ink-jet. Therefore, significant cost reduction may be realized by fabricating a semiconductor device using the organic semiconductor material, compared to a case where the inorganic semiconductor material is used to fabricate.

Japanese published unexamined patent application No. 2006-37098 proposes, as a semiconductor material, an organic semiconductor polymer, which simultaneously shows p-type and n-type electric characteristics by alternately containing an oligothiophene that has the p-type semiconductor characteristic, and an aromatic heterocyclic ring that has the n-type semiconductor characteristic in a polymer main chain.

Japanese published unexamined patent application No. 2006-117672 proposes an oligothiophene-allylene derivative that introduces an allylene having a n-type semiconductor characteristic to an oligothiophene unit having a p-type semiconductor characteristic.

However, the carrier mobility of such a conventional organic semiconductor material is not sufficient, and there has been a demand for new organic semiconductor materials with higher carrier mobility. Further, the on/off ratio, which is a ratio of the current in an on-state and the current is an off-state, is not sufficient when used as an organic transistor, therefore, there has been a demand for a new organic semiconductor material which demonstrates a higher on/off ratio.

Further, there has been a demand for an organic semiconductor material capable of easily controlling a threshold voltage Vth, which is a voltage that transits the on-state and the off-state, to a predetermined voltage in a case when used as an organic field effect transistor.

Further, there has been a demand for an organic semiconductor material capable of dissolving in an inexpensive organic solvent with an adequate volatility in a case when forming a semiconductor layer by the printing method such as ink-jet.

SUMMARY OF THE INVENTION

The objective of the present invention is to provide an organic semiconductor material with a high carrier mobility, capable of obtaining favorable semiconductor characteristics in a case when used in an organic semiconductor device, and an organic transistor using the same.

The organic semiconductor material according to the present invention is characterized by having a following structure, includes an oligothiophene part and a connecting part G.

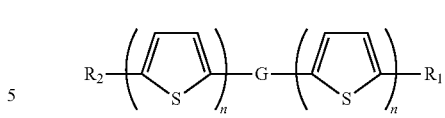
[Formula 1]

In the formula, $R_1$ and $R_2$ are a hydrogen, an alkyl group which is unsubstituted or substituted by one or more substituents, an alkoxy group which is unsubstituted or substituted by one or more substituents, an aryl group which is unsubstituted or substituted by one or more substituents, or an alkenyl group which is unsubstituted or substituted by one or more substituents. $R_1$ and $R_2$ may be identical or different from each other, and n is an integer.

And the connecting part G has any of the following structures:

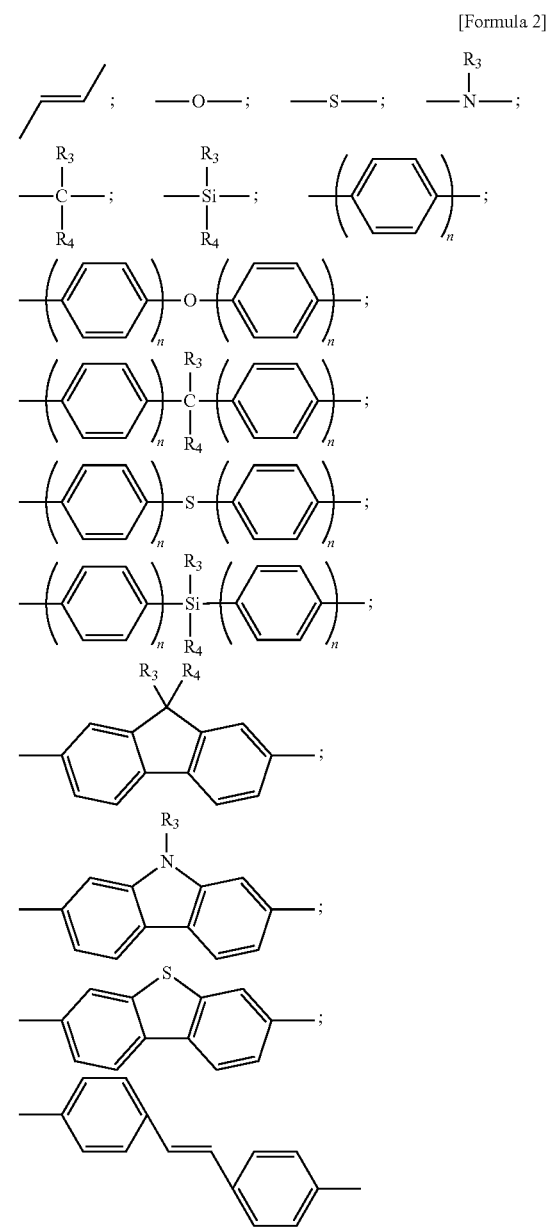
[Formula 2]

In the formula, $R_3$ and $R_4$ are a hydrogen, an alkyl group which is unsubstituted or substituted by one or more substituents, an alkoxy group which is unsubstituted or substituted by one or more substituents, an aryl group which is unsubstituted or substituted by one or more substituents, or an alkenyl group which is unsubstituted or substituted by one or more substituents. $R_3$ and $R_4$ may be identical or different from each other, and n is an integer of 1 to 3.

By having the chemical structure described above, the organic semiconductor material according to the present invention has a high carrier mobility. Also, a high on/off ratio is shown in a case when used in an organic semiconductor device, such as an organic transistor. Further, the transistor characteristics that are superior in controllability of threshold voltage and so on may be obtained.

The organic semiconductor material according to the present invention is soluble in an inexpensive organic solvent, such as chloroform or an aromatic solvent, that shows an adequate volatility. For this reason, a semiconductor layer can easily be formed by a printing method, such as ink-jet.

The molar mass of the connecting part G is preferably approximately less than 5000. By maintaining the molar mass approximately less than 5000, the solubility against the solvent can further be increased.

The connecting part G is further preferably in following structures:

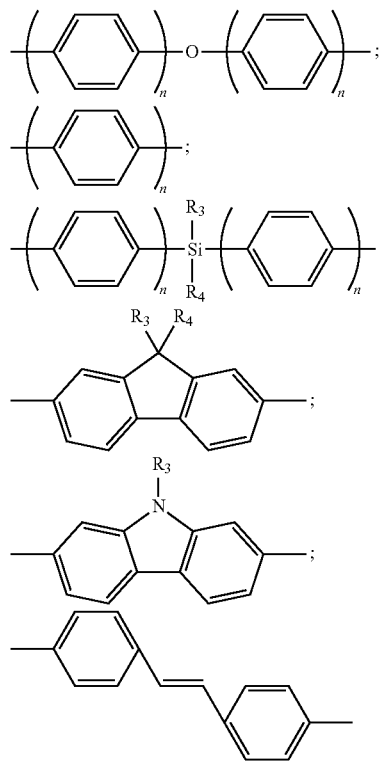

[Formula 3]

In the formula, $R_3$ and $R_4$ are a hydrogen, an alkyl group which is unsubstituted or substituted by one or more substituents, an alkoxy group which is unsubstituted or substituted by one or more substituents, an aryl group which is unsubstituted or substituted by one or more substituents, or an alkenyl group which is unsubstituted or substituted by one or more substituents, $R_3$ and $R_4$ may be identical or different from each other, and n is an integer of 1 to 3.

In the structural formula above, $R_1$ and $R_2$ are preferably carbon number 4 or more, further preferably carbon number 4 to 20. Further $R_1$ and $R_2$ are preferably carbon number ranging from 4 to 12, and further preferably carbon number ranging from 4 to 8. Furthermore, $R_1$ and $R_2$ are preferably carbon number 4 or more, but may range from carbon number 4 to 20, but may also comprise an alkyl group which is unsubstituted or substituted by one or more substituents.

Further, n, which indicates the number of repeat unit of thiophene, is preferably 3 to 11, and n is further preferably odd numbers. Therefore, n, which indicates the number of repeat unit of thiophene, is further preferably 3, 5, 7, 9 or 11.

$R_3$ and $R_4$ at the connecting part G are preferably carbon numbers that may range from carbon 1 to 20. $R_3$ and $R_4$ are further preferably carbon number ranging from 1 to 12, and most preferably carbon number ranging from 1 to 8. Further, $R_3$ and $R_4$ are preferably an alkyl group which is unsubstituted or substituted by one or more substituents, or an aryl group which is unsubstituted or substituted by one or more substituents.

Further, in the present invention, the oligothiophene part may be a thiophene derivative having the following structure:

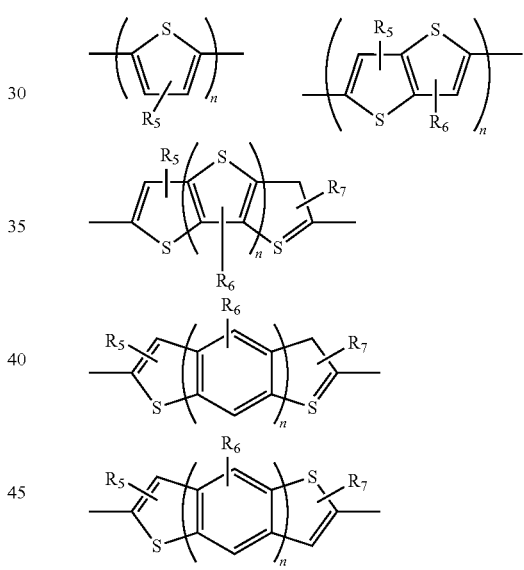

[Formula 4]

In the formula, $R_5$, $R_6$ and $R_7$ are a hydrogen, or an alkyl group which is unsubstituted or substituted by one or more substituents, an alkoxy group which is unsubstituted or substituted by one or more substituents, an aryl group which is unsubstituted or substituted by one or more substituents, or an alkenyl group which is unsubstituted or substituted by one or more substituents. $R_5$, $R_6$ and $R_7$ may be identical or different from each other, and n is an integer preferably of 3 to 11, and further preferably 3, 5, 7, 9, or 11.

The organic transistor according to the present invention is characterized by having an organic semiconductor material according to the present invention described above.

The field effect transistor according to the present invention includes a semiconducting layer and a gate electrode, which directly or indirectly contacts the semiconducting layer, and the current in the semiconducting layer is controlled by impressing an electric field between the gate electrode and the semiconducting layer. In the field effect transistor, the semiconducting layer includes the organic semiconductor material according the present invention.

Because the organic transistor and the field effect transistor according to the present invention use the organic semiconductor material according to the present invention, the on/off ratio is high and is superior in controllability of the threshold voltage and so on.

The organic semiconductor material according to the present invention has a high carrier mobility, thus favorable semiconductor characteristics may be obtained when used in an organic semiconductor device.

A method for fabricating an organic material according to the present invention may include the steps of reacting, in the presence of a metallic catalyst and a base, a first compound having a following structure indicated in the formula 5, that includes a connecting part G:

[Formula 5]

X-G-X  (5)

In the formula 5, X is an iodine, a bromine, or a chlorine, which may be identical or different from each other. Further, G in the formula 5 has any of the following structures indicated in formula 6:

[Formula 6]

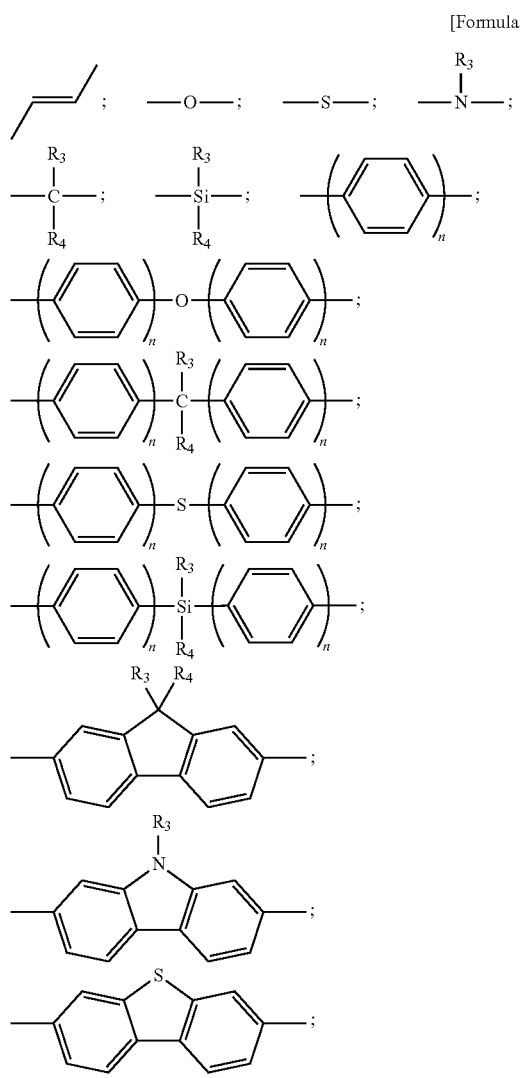

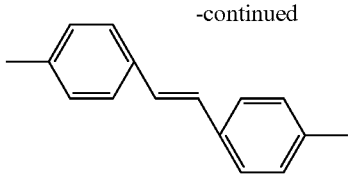

In the formula 6, $R_3$ and $R_4$ are a hydrogen, an alkyl group which is unsubstituted or substituted by one or more substituents, an alkoxy group which is unsubstituted or substituted by one or more substituents, an aryl group which is unsubstituted or substituted by one or more substituents, or an alkenyl group which is unsubstituted or substituted by one or more substituents. $R_3$ and $R_4$ may be identical or different from each other, and n is an integer of 1 to 3; and reacting the above compound with a second compound having a following structure indicated in formula 7:

[Formula 7]

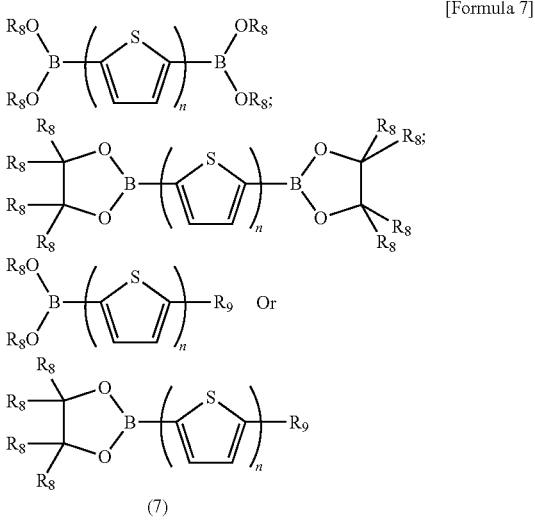

(7)

In the formula 7, $R_8$ and $R_9$ are a hydrogen or an alkyl group which is unsubstituted or substituted by one or more substituents. $R_8$ and $R_9$ may be identical or different from each other, and n is an integer.

In the fabrication method, the metallic catalyst may be a palladium. The compounds may be heated at approximately 85 degree/C. to 100 degree/C. for reaction. The reaction time may be approximately 1 to 5 hours.

In the fabrication method, the molar mass of the connecting part G may be approximately less than 5000.

In the fabrication method, the connecting part G may be in any of following structures:

[Formula 8]

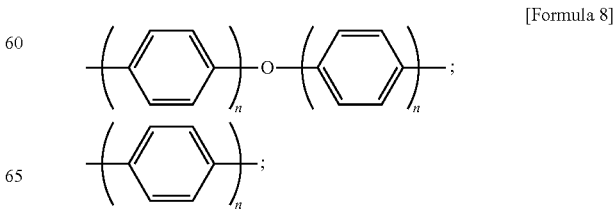

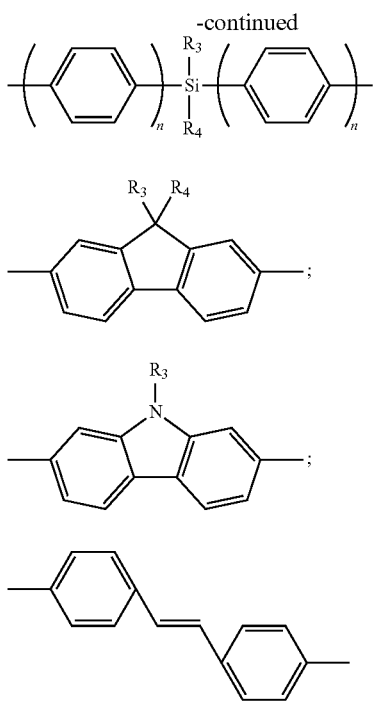

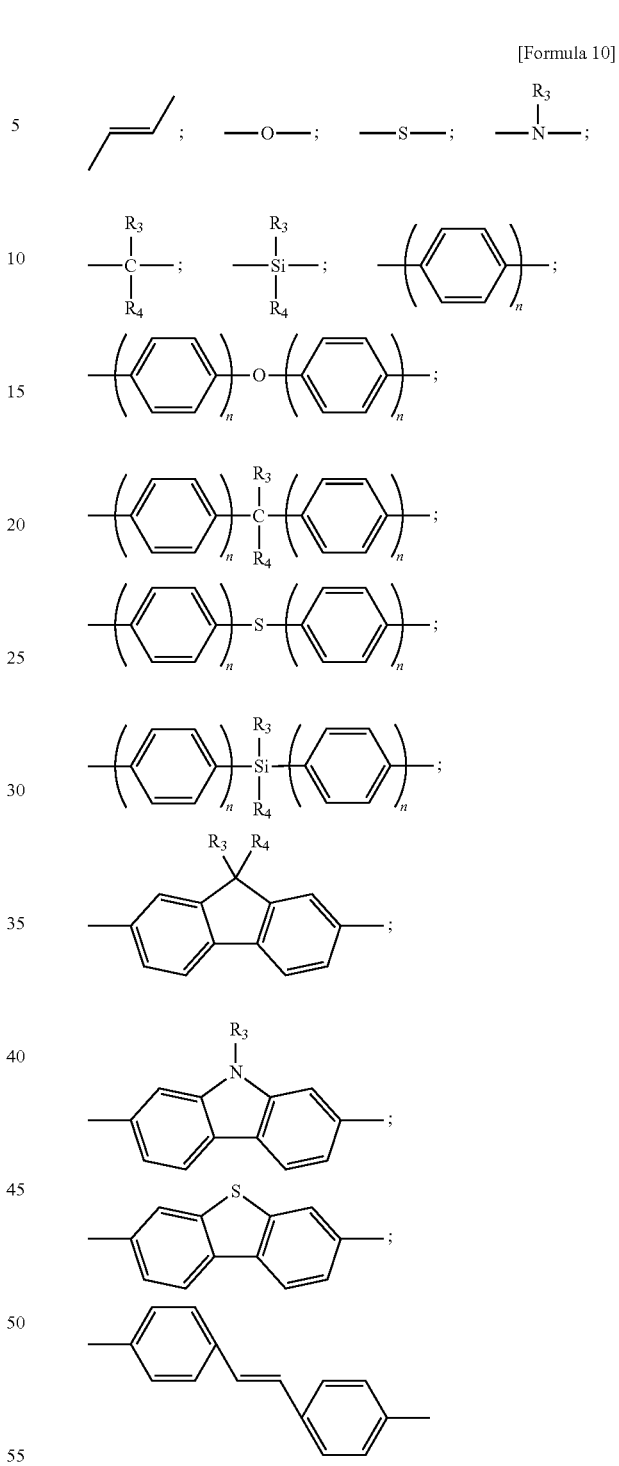

In the formula 8, $R_3$ and $R_4$ are a hydrogen, an alkyl group which is unsubstituted or substituted by one or more substituents, an alkoxy group which is unsubstituted or substituted by one or more substituents, an aryl group which is unsubstituted or substituted by one or more substituents, or an alkenyl group which is unsubstituted or substituted by one or more substituents. $R_3$ and $R_4$ may be identical or different from each other, and n is an integer of 1 to 3.

In the fabrication method, $R_3$ and $R_4$ may be an alkyl group of carbon number 4 or more, or may be unsubstituted or substituted by one or more substituents.

Another method for fabricating an organic material according to the present invention may include the steps of reacting, in the presence of a metallic catalyst and a base, a first compound having a following structure indicated in formula 9, includes a connecting part G:

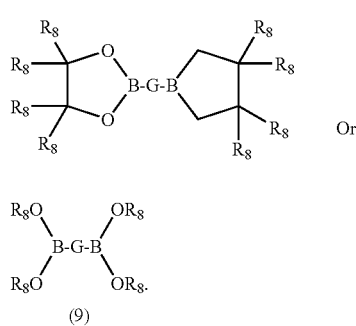

In the formula 9, $R_8$ is a hydrogen or an alkyl group which is unsubstituted or substituted by one or more substituents, and $R_8$ may be identical or different from each other. Further, G in the formula 9 has any of the following structures indicated in formula 10:

In the formula 10, $R_3$ and $R_4$ are a hydrogen, an alkyl group which is unsubstituted or substituted by one or more substituents, an alkoxy group which is unsubstituted or substituted by one or more substituents, an aryl group which is unsubstituted or substituted by one or more substituents, or an alkenyl group which is unsubstituted or substituted by one or more substituents. $R_3$ and $R_4$ may be identical or different from each other, and n is an integer of 1 to 3; and reacting the above compound with a second compound having the following structures indicated in formula 11:

[Formula 11]

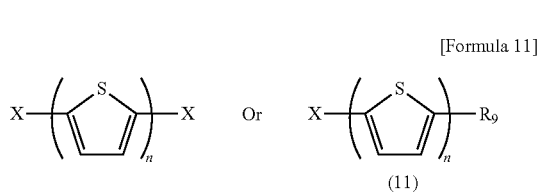

(11)

In the formula 11, X is an iodine, a bromine, or a chlorine, X may be identical or different from each other. Further, in the formula 11, $R_9$ is a hydrogen or an alkyl group which is unsubstituted or substituted by one or more substituents. And, in the formula 11, n is an integer.

In the fabrication method, the metallic catalyst may be a palladium. The compound may be heated at approximately 85 degree/C. to 100 degree/C. for reaction. The reaction time may be approximately 1 to 5 hours. The molar mass of the connecting part G may be approximately less than 5000. In the formulas described above, $R_5$, $R_6$, and $R_7$ are preferably carbon number ranging from 1 to 20, further preferably carbon number ranging from 1 to 12, and most preferably, carbon number ranging from 3 to 8. Meanwhile, the carbon number of $R_8$ preferably ranges from 1 to 8, and further preferably ranges from 1 to 3. Meanwhile, the carbon number of $R_9$ preferably ranges from 1 to 20, further preferably, it may range from 4 to 12, and most preferably, ranges from 4 to 8. Further, with respect to the $R_1$ to $R_9$, the substituents that may be contained in the alkyl group, the alkoxy group, the aryl group, or the alkenyl group are not limited specifically, and it may be an alkyl group, an alkoxy group, an aryl group, or an alkenyl group. These substituents may be the same or different from each other.

DETAILED DESCRIPTION OF INVENTION

Figure 1:
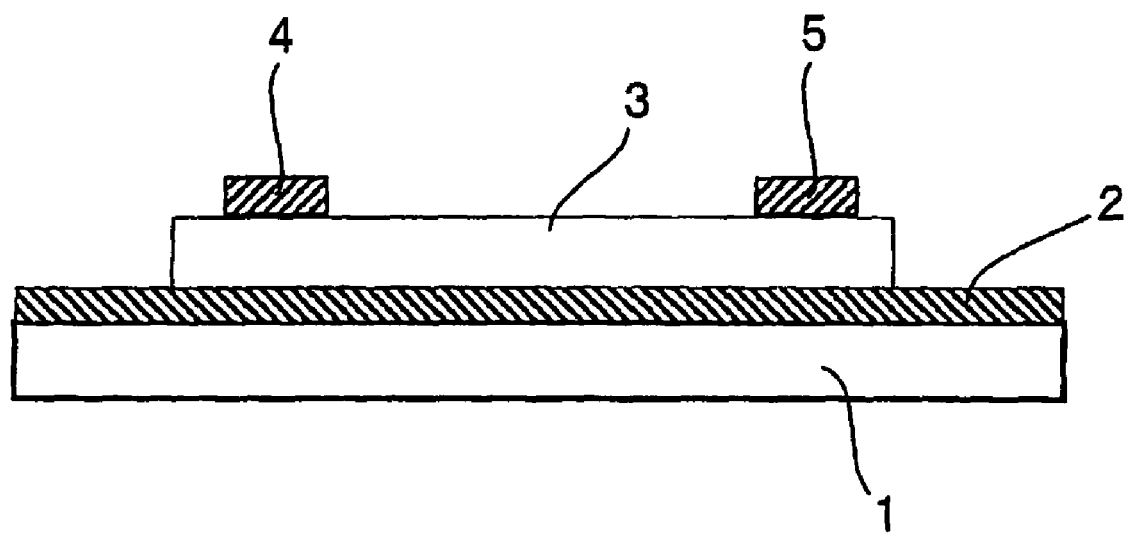
FIG. 1 is a schematic cross-sectional view of an organic transistor fabricated by an embodiment according to the present invention.

The present invention is hereinafter explained with reference to specific embodiments, however, the present invention is not limited to the embodiments below.

Synthesis of Embodiment 1

4-(5''''-n-hexyl-pentathiophene-2-yl)phenylether [Compound 1]

[Formula 12]

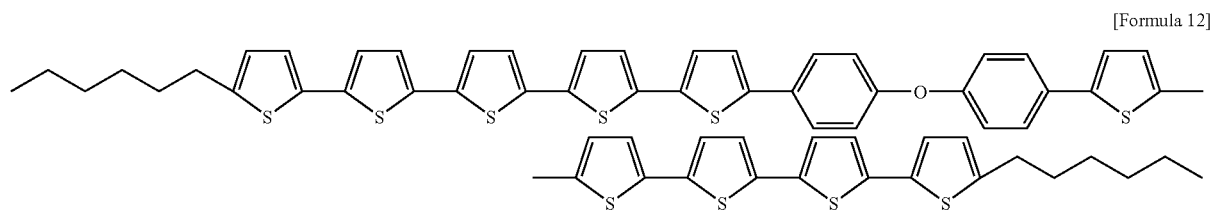

In a dry closed reaction chamber provided with a mechanical agitator and nitrogen/vacuum inlets connected to a nitrogen line and a vacuum line, add 4,4'-dibromodiphenyl ether (82 mg, 0.25 mmol), 5,5'-di(4,4,5,5-tetramethyl-1,3,2,-dioxaborolan-2-yl)-2,2'-bithiophene (209 mg, 0.5 mmol), Suzuki coupling catalyst, 20 ml of anisole and 8 ml of base solution for reaction. The temperature of the reaction chamber is increased to 95 degree/C. after repeating for three times a decompression-nitrogen substitution operation. The reaction is performed for approximately 4 hours at 95 degree/C. under a nitrogen atmosphere. Next, add 2,5-diiode thiophene (168 mg, 0.5 mmol) and continue the reaction for three more hours at 95 degree/C. under a nitrogen atmosphere. Thereafter, add 5-(4,4,5,5-tetramethyl-dioxaborolan-2-yl)-5'-n-hexyl-2,2'-bithiophene (207 mg, 0.55 mmol) and further continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a yellow-brown powder is obtained. The yield is 43%.

Synthesis of Embodiment 2

9-n butyl-3,6-di(5''''-n-hexyl-pentathiophene-2-yl) carbazole [Compound 2]

[Formula 13]

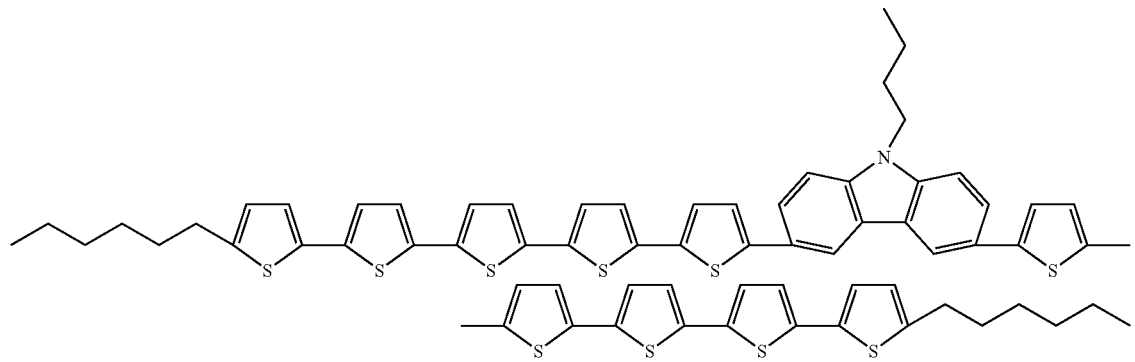

In a dry closed reaction chamber provided with a mechanical agitator and nitrogen/vacuum inlets connected to a nitrogen line and a vacuum line, add 9-buthyl-3,6-dibromocarbazole (189.5 mg, 0.5 mmol), 5,5'-di(4,4,5,5-tetramethyl-1,3,2-dioxaborolan-2-yl)-2,2'-bithiophene (418 mg, 1 mmol), Suzuki coupling catalyst, 5 ml of toluene and 8 ml of a base solution for reaction. The temperature of the reaction chamber is increased to 95 degree/C. after repeating for three times a decompression-nitrogen substitution operation. The reaction is performed for approximately 4 hours at 95 degree/C. under a nitrogen atmosphere. Next, add 2,5-diiode thiophene (336 mg, 1 mmol) and continue the reaction for three more hours at 95 degree/C. under a nitrogen atmosphere. Thereafter, add 5-(4,4,5,5-tetramethyl-1,3,2-dioxaborolan-2-yl)-5'-n-hexyl-2,2'-bithiophene (414 mg, 1.1 mmol) and further continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a yellow powder is obtained. The yield is 23%.

Synthesis of Embodiment 3

Methyl-[4,4'-di(5''''-n-hexyl-pentathiophene-2-yl) triphenylsilane [Compound 3]

[Formula 14]

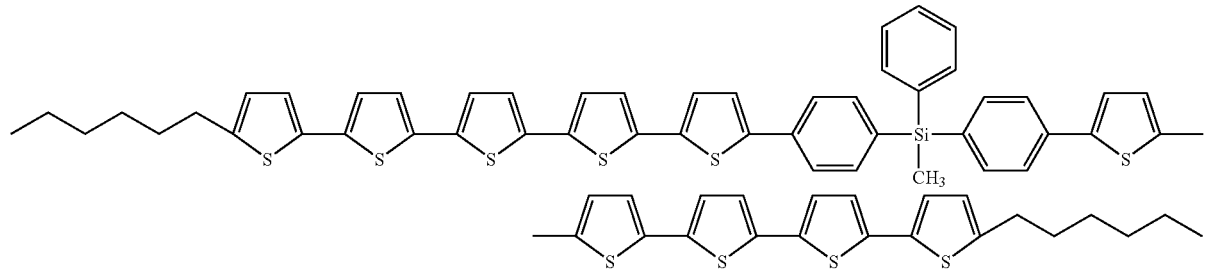

Add methyl-4,4'-dibromotriphenylsilane (216 mg, 0.5 mmol), 5,5'-di(4,4,5,5-tetramethyl-1,3,2,-dioxaborolan-2-yl)-2,2'-bithiophene (418 mg, 1 mmol), Suzuki coupling catalyst, 5 ml of toluene and 8 ml of a base solution for reaction. The temperature of the reaction chamber is increased to 95 degree/C. after repeating for three times a decompression-nitrogen substitution operation. The reaction is performed for approximately 4 hours at 95 degree/C. under a nitrogen atmosphere. Next, add 2,5-diiode thiophene (336 mg, 1 mmol) and continue the reaction for three more hours at 95 degree/C. under a nitrogen atmosphere. Thereafter, add 5-(4,4,5,5-tetramethyl-1,3,2-dioxaborolan-2-yl)-5'-n-hexyl-2,2'-bithiophene (414 mg, 1.1 mmol) and further continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a yellow powder is obtained. The yield is 29%.

Synthesis of Embodiment 4

4,4'-di(5''''-n-hexyl-pentathiophene-2-yl)stilbene [Compound 4]

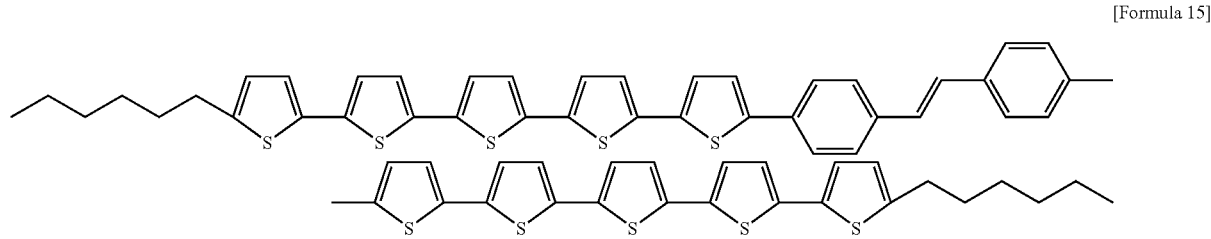

[Formula 15]

Add 4,4'-dibromostilbene (169 mg, 0.5 mmol), 5,5'-di(4,4,5,5-tetramethyl-1,3,2,-dioxaborolan-2-yl)-2,2'-bithiophene (418 mg, 1 mmol), Suzuki coupling catalyst, 5 ml of toluene and 8 ml of a base solution for reaction. The temperature of the reaction chamber is increased to 95 degree/C. after repeating for three times a decompression-nitrogen substitution operation. The reaction is performed for approximately 4 hours at 95 degree/C. under a nitrogen atmosphere. Next, add 2,5-diiode thiophene (336 mg, 1 mmol) and continue the reaction for three more hours at 95 degree/C. under a nitrogen atmosphere. Thereafter, add 5-(4,4,5,5-tetramethyl-1,3,2-dioxaborolan-2-yl)-5'-n-hexyl-2,2'-bithiophene (414 mg, 1.1 mmol) and further continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a blackish brown powder is obtained. The yield is 34%.

Synthesis of Embodiment 5

9,9-dioctyl-2,7-di(5''''-n-hexyl-pentathiophene-2-yl) fluorene [Compound 5]

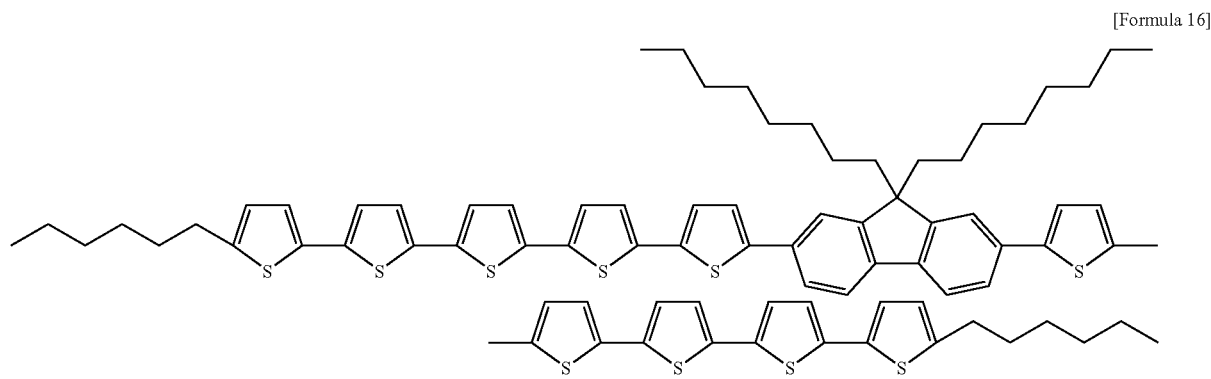

[Formula 16]

Add 2,5'-diiodethiophene (336 mg, 1 mmol), 2,5-diboronic acid thiophene (86 mg, 0.5 mmol), Suzuki coupling catalyst, 10 ml of anisole and 8 ml of a base solution for reaction. The temperature of the reaction chamber is increased to 95 degree/C. after repeating for three times a decompression-nitrogen substitution operation. The reaction is performed for approximately 4 hours at 95 degree/C. under a nitrogen atmosphere. Next, add 9,9-dioctyl-2,7-di(4,4,5,5-tetramethyl-1,3,2-dioxaborolan-2-yl) fluorene (160.5 mg, 0.25 mmol) and continue the reaction for three more hours at 95 degree/C. under a nitrogen atmosphere. Thereafter, add 5-(4,4,5,5-tetramethyl-1,3,2-dioxaborolan-2-yl)-5'-n-hexyl-2,2'-bithiophene (207 mg, 0.55 mmol) and further continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a blackish brown powder is obtained. The yield is 72%.

Synthesis of Embodiment 6

1,4-di(5''''-n-hexyl-trithiophene-2-yl)benzene [Compound 6]

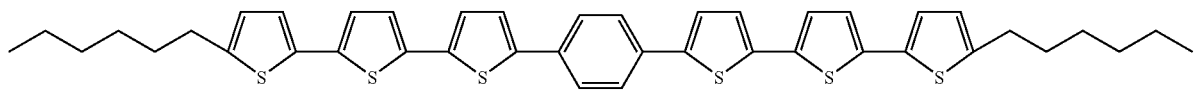

[Formula 17]

Add 2,5'-diiodethiophene (336 mg, 1 mmol), 1,4-di(4,4,5,5-tetramethyl-1,3,2-dioxaborolan-2-yl)benzene (165 mg, 0.5 mmol), Suzuki coupling catalyst, 20 ml of anisole and 8 ml of base solution for reaction. The temperature of the reaction chamber is increased to 95 degree/C. after repeating for three times a decompression-nitrogen substitution operation. The reaction is performed for approximately 4 hours at 95 degree/C. under a nitrogen atmosphere. Next, add 5-(4,4,5,5-tetramethyl-1,3,2-dioxaborolan-2-yl)-5'-n-hexyl-2,2'-bithiophene (207 mg, 0.55 mmol) and continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a yellow-brown powder is obtained. The yield is 34%.

Synthesis of Embodiment 7

4,4'-di(5''''-n-hexyl-pentathiophene-2-yl)biphenyl [Compound 7]

Add 4,4'-diiodebiphenyl (101.5 mg, 0.25 mmol), 5,5'-di(4,4,5,5-tetramethyl-1,3,2-dioxaborolan-2-yl)-2,2'-bithiophene (209 mg, 0.5 mmol), Suzuki coupling catalyst, 20 ml of anisole and 8 ml of a base solution for reaction. The temperature of the reaction chamber is increased to 95 degree/C. after repeating for three times a decompression-nitrogen substitution operation. The reaction is performed for approximately 3 hours at 95 degree/C. under a nitrogen atmosphere. Next, add 2,5-diiodethiophene (168 mg, 0.5 mmol) and continue the reaction for three more hours at 95 degree/C. under a nitrogen atmosphere. Thereafter, add 5-(4,4,5,5-tetramethyl-1,3,2-dioxaborolan-2-yl)-5'-n-hexyl-2,2'-bithiophene (207 mg, 0.55 mmol) and further continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a yellow-brown powder is obtained. The yield is 33%.

[Formula 18]

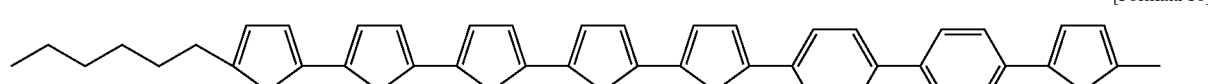

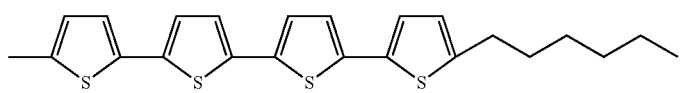

Synthesis of Embodiment 8

9,9(dimethyloctylsilyl)-2,7-di(5''''-n-hexyl-pentathiophene-2-yl) fluorene [Compound 8]

[Formula 19]

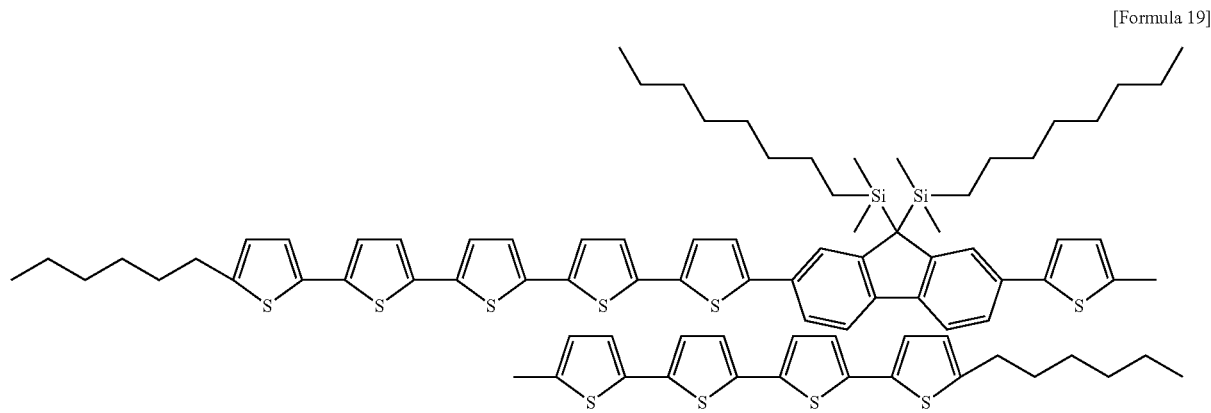

Add 9,9'-di(dimethyloctylsilyl)-2,7-dibromofluorene (332 mg, 0.5 mmol), 5,5'-di(4,4,5,5-tetramethyl-1,3,2-dioxaborolan-2-yl)-2,2'-bithiophene (418 mg, 1 mmol), Suzuki coupling catalyst, 5 ml of toluene and 8 ml of a base solution for reaction. The temperature of the reaction chamber is increased to 95 degree/C. after repeating for three times a decompression-nitrogen substitution operation. The reaction is performed for approximately 3 hours at 95 degree/C. under a nitrogen atmosphere. Next, add 2,5-diiodethiophene (336 mg, 1 mmol) and continue the reaction for three more hours at 95 degree/C. under a nitrogen atmosphere. Thereafter, add 5-(4,4,5,5-tetramethyl-1,3,2-dioxaborolan-2-yl)-5'-n-hexyl-2,2'-bithiophene (414 mg, 1.1 mmol) and further continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a brown powder is obtained. The yield is 26%.

[Fabrication of an Organic Transistor]

A MOS type field effect transistor is fabricated using the organic semiconductor material fabricated as described above.

FIG. 1 is a schematic cross-sectional view showing a structure of the fabricated MOS type field effect transistor. As shown in FIG. 1, an insulating layer 2 consists of a dielectric that is located on the surface of a gate electrode 1, an organic semiconductor layer 3 is formed on the insulating layer 2, and a source electrode 4 and a drain electrode 5 are formed apart from each other in a predetermined distance on the organic semiconductor layer 3.

Figure 2:
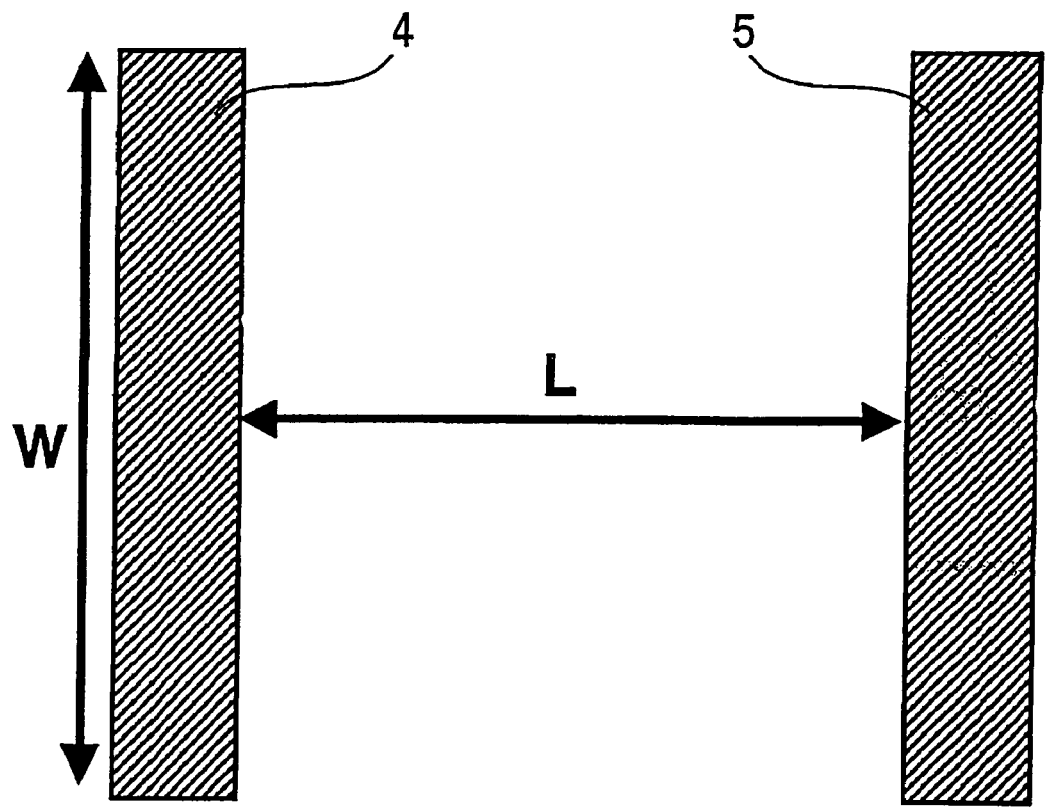
FIG. 2 is a plane view of a source electrode and a drain electrode in the organic transistor of FIG. 1.

FIG. 2 is a plane view showing the source electrode 4 and the drain electrode 5. As shown in FIG. 2, a distance L between the source electrode 4 and the drain electrode 5 is regarded as a channel length, and each width of the source electrode 4 and drain electrode 5 is regarded as a channel width W.

In the organic transistor shown in FIG. 1, a silicon wafer 1, which is n doped in a high-concentration, is used as the gate electrode. Onto this silicon wafer 1, formed is the insulating layer 2 consisting of a silicon dioxide, in a layer thickness of 100 nm. The silicone wafer 1 is used after performing an ultrasonic cleaning in an order of a 2-propanol, acetone, ion-exchanged water, and methanol, and then the surface is washed by an ultraviolet and ozone treatment. Onto the insulating layer 2, the organic semiconductor layer 3 is formed in a layer thickness of 100 nm to 150 nm.

The organic semiconductor layer 3 is formed as follows. Prepare a solution by dissolving the organic semiconductor material with an inexpensive organic solvent with an adequate volatility (chloroform), spin coating this solution onto the surface of insulating layer 2, and baking at 80 degree/C. for one hour under a reduced pressure in a vacuum oven to remove the organic solvent. The organic semiconductor layer 3 is formed in this way.

Onto the organic semiconductor layer 3, formed are a source electrode 4 and a drain electrode 5 consisting of gold by vacuum deposition.

The transistor characteristics between the three terminals, the gate electrode 1, the source electrode 4, and the drain electrode 5 on silicon wafer 1, were measured by using Agilent Technologies' 4156C Precision Semiconductor Parameter Analyzer at a room temperature (approximately 20 degree/C.) under an approximately standard atmosphere.

Embodiment 1

The characteristics of the organic transistor (the MOS type field effect transistor) obtained as described above by forming the organic semiconductor layer 3 using the compound 1 is evaluated as described above. The channel length L is 0.05 mm and the channel width W is 1 mm.

Figure 3:
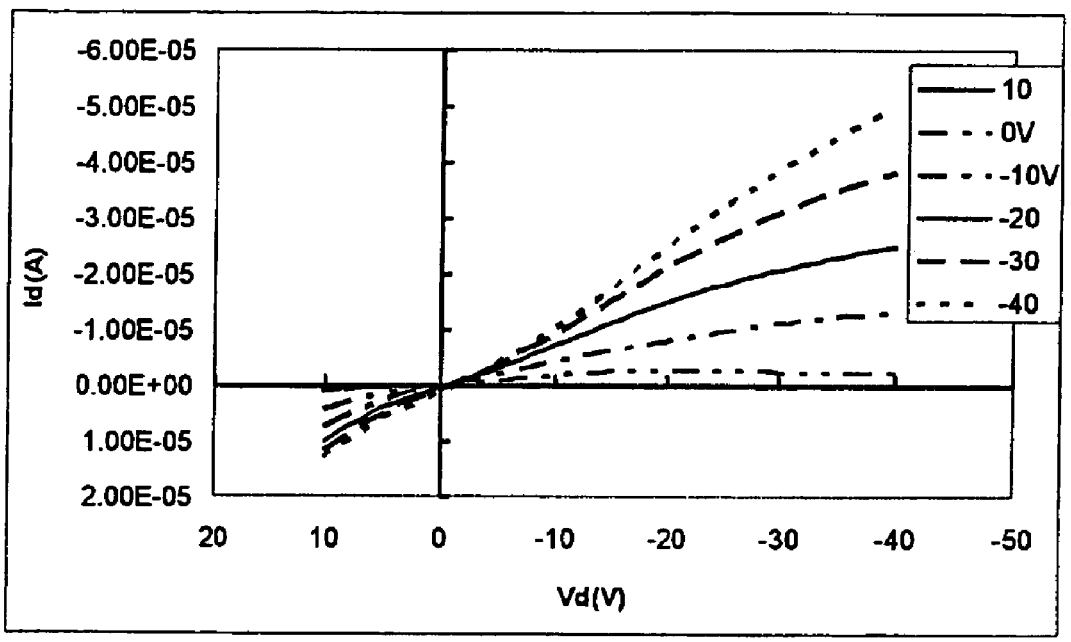
FIG. 3 shows V-I characteristics of an organic transistor fabricated in embodiment 1.
Figure 4:
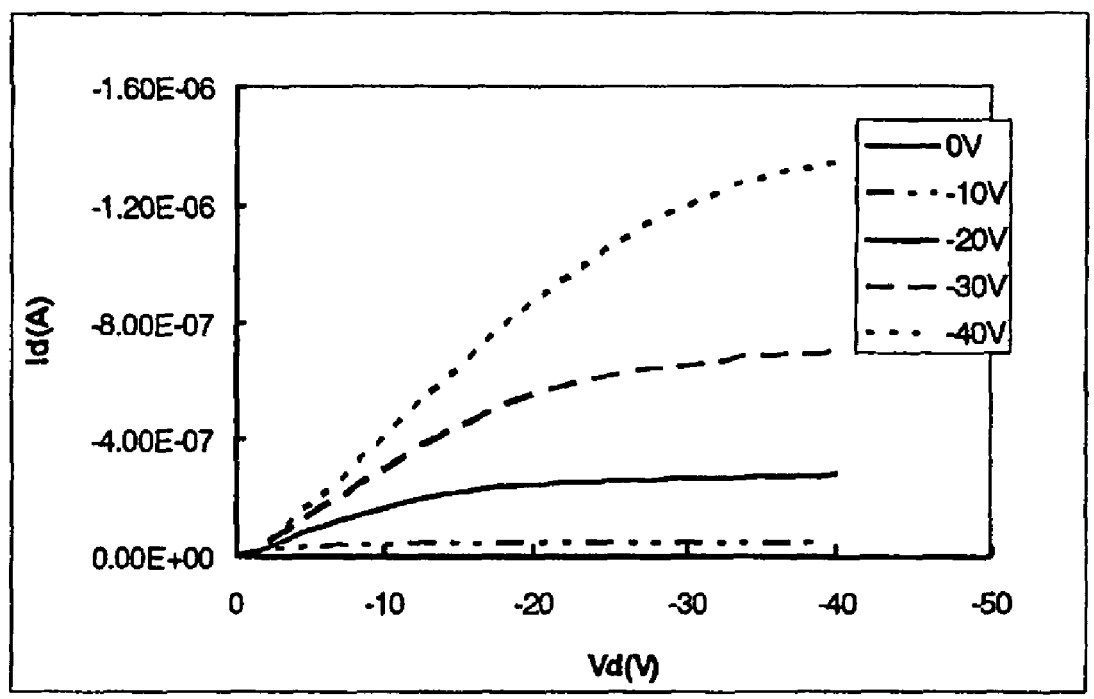
FIG. 4 shows V-I characteristics of an organic transistor fabricated in embodiment 2.
Figure 5:
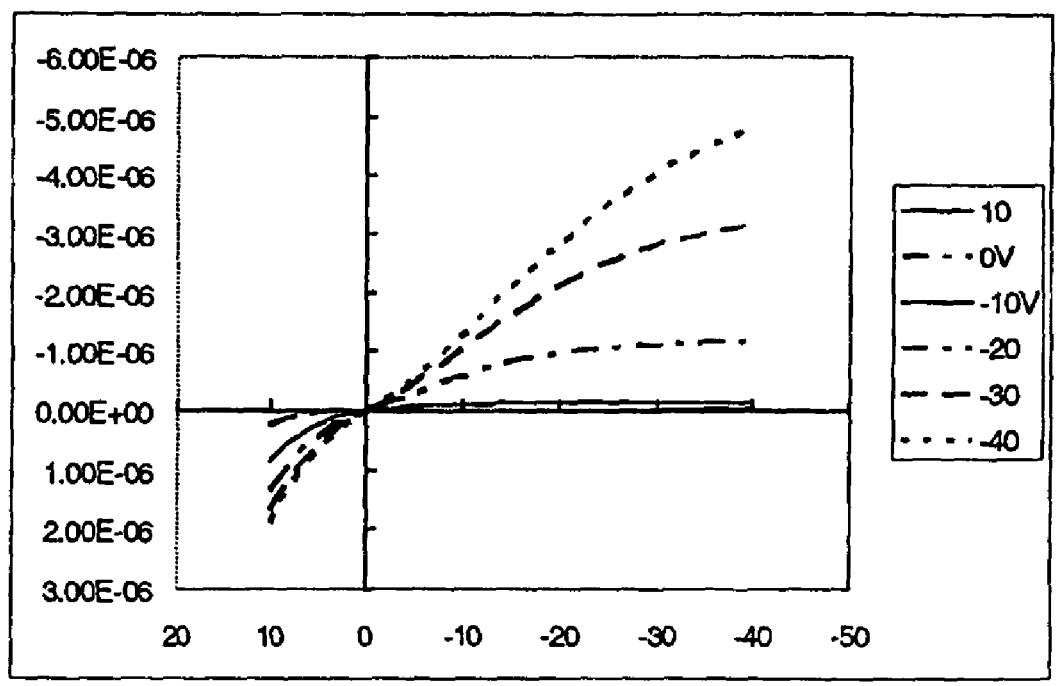
FIG. 5 shows V-I characteristics of an organic transistor fabricated in embodiment 3.
Figure 6:
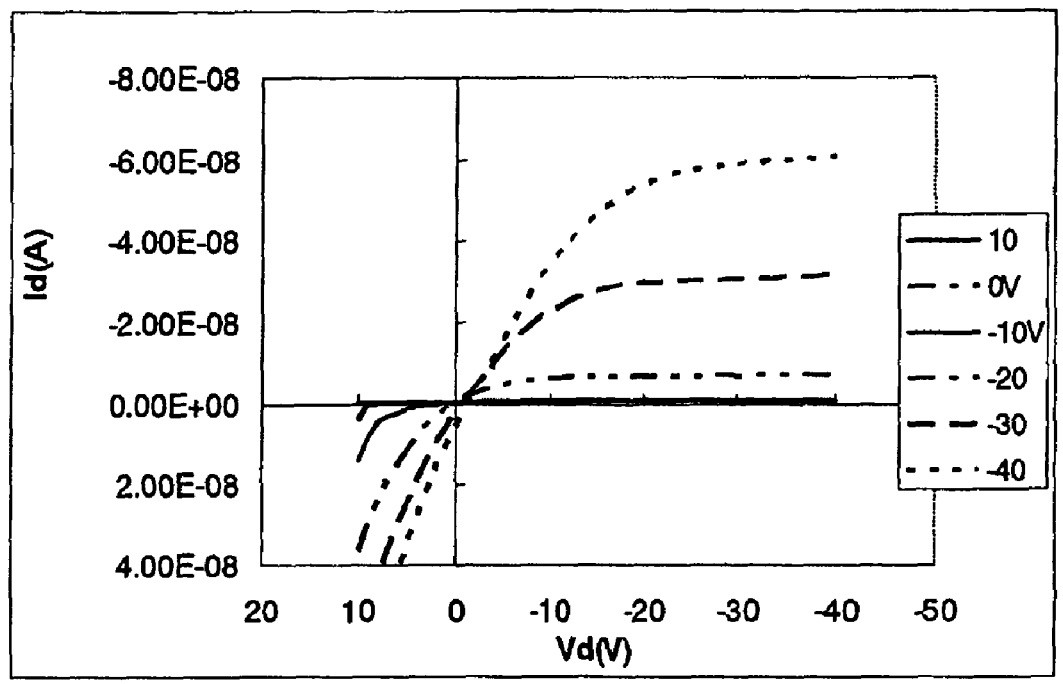
FIG. 6 shows V-I characteristics of an organic transistor fabricated in embodiment 4.
Figure 7:
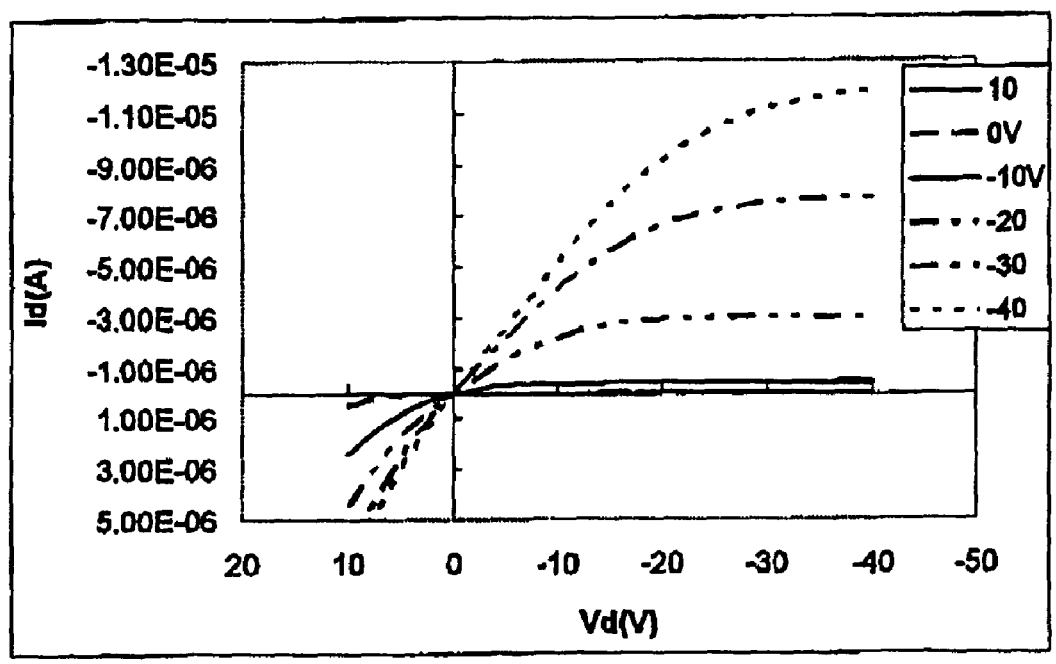
FIG. 7 shows V-I characteristics of an organic transistor fabricated in embodiment 5.
Figure 8:
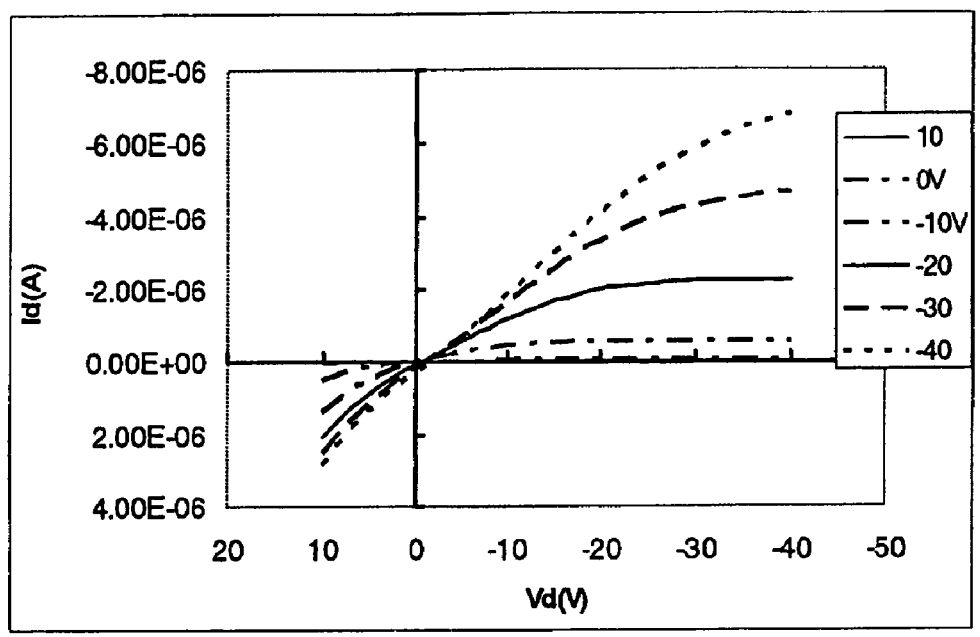
FIG. 8 shows V-I characteristics of an organic transistor fabricated in embodiment 6.
Figure 9:
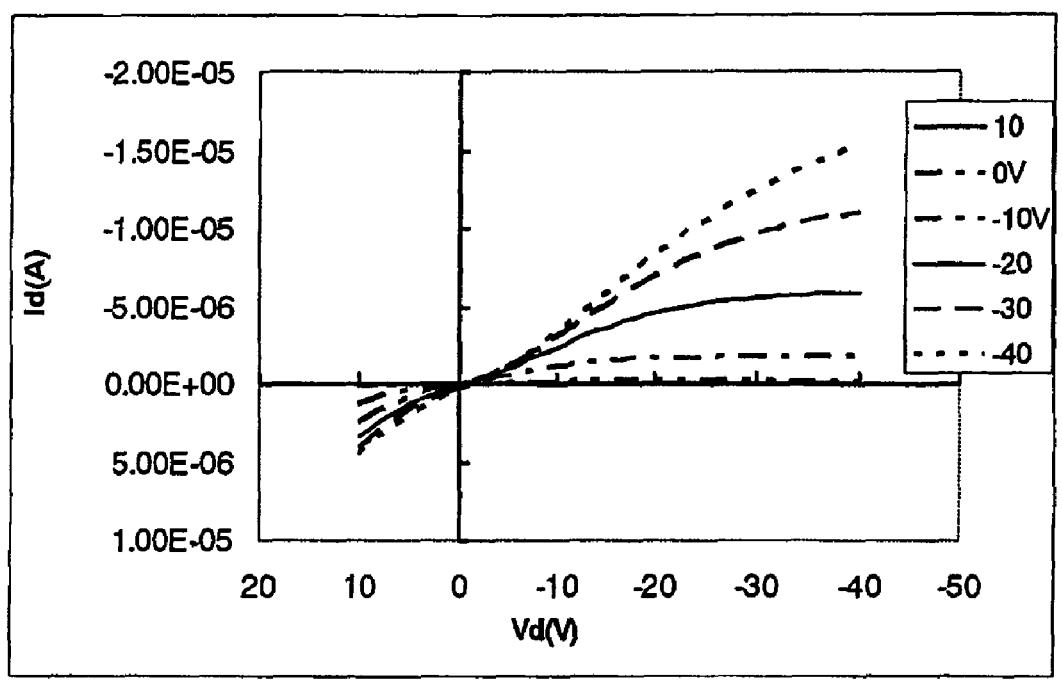
FIG. 9 shows V-I characteristics of an organic transistor fabricated in embodiment 7.
Figure 10:
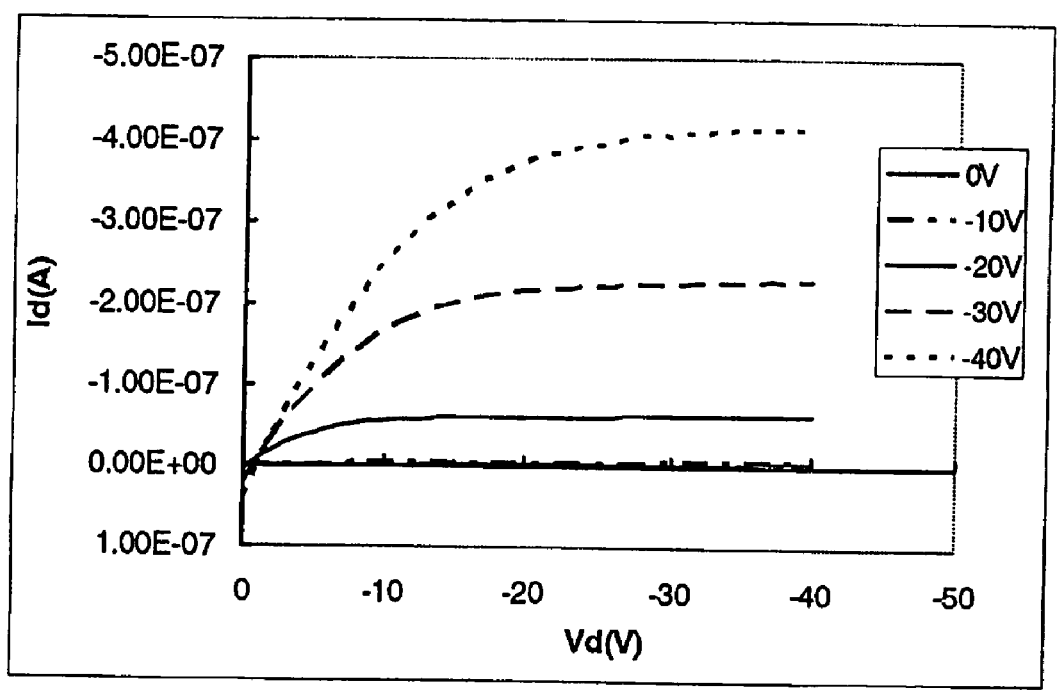
FIG. 10 shows V-I characteristics of an organic transistor fabricated in embodiment 8.

FIG. 3 shows V-I characteristics. The On/Off ratio is 1056, the mobility is 0.0775 $cm^2/Vs$, and favorable transistor characteristics are obtained. The threshold voltage Vth, which is a voltage that the on state and the off state of the organic field effect transistor transits, can easily be controlled to a predetermined voltage, the average is 8.5V, and the variation is very small.

Embodiments 2 to 8

The above transistors are fabricated as described in the embodiment 1 above using the compounds 2 to 8, and evaluations are also performed as described above. The channel lengths L and the channel widths W are as shown in table 1. Further, the V-I characteristics of each transistor is as shown in FIGS. 4 to 10. The evaluation results are summarized in table 1. Also, the table 1 shows the result of the embodiment 1.

TABLE 1

| Compound | Channel Length L (mm) | Channel Width W (mm) | On/Off Ratio | Mobility ($cm^2/Vs$) | Threshold Voltage Vth (V) |
|---|---|---|---|---|---|
| Compound 1 | 0.05 | 1 | 1056 | 0.0775 | 8.47 |
| Compound 2 | 0.05 | 1 | 707 | 0.0049 | −9.4 |
| Compound 3 | 0.05 | 1 | 185 | 0.018 | 1.35 |
| Compound 4 | 0.05 | 1 | 84 | 0.00054 | −6.04 |
| Compound 5 | 0.05 | 1 | 39063 | 0.0422 | −8.84 |
| Compound 6 | 0.05 | 1 | 4160 | 0.0185 | −3.12 |
| Compound 7 | 0.05 | 1 | 5492 | 0.0375 | −0.47 |
| Compound 8 | 0.05 | 1 | 101 | 0.0034 | −16 |

As shown in table 1 and FIGS. 4 to 10, high on/off ratios and motilities are obtained, and favorable transistor characteristics are obtained. Also, the threshold voltage Vth can easily be controlled, and the variation was very small.

Comparative Example 1

An organic transistor is fabricated with the embodiment described above using P3HT as indicated in the following structural formula:

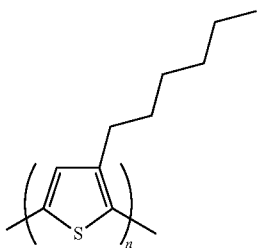

[Formula 20]

The channel length L is 0.2 mm and the channel width W is 1 mm.

Figure 11:
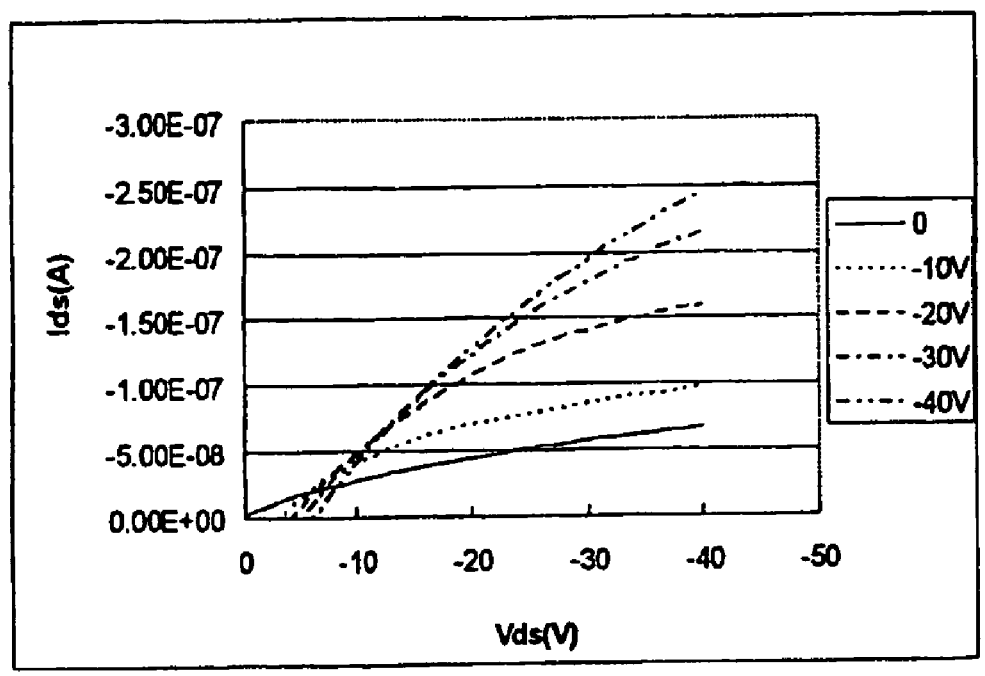
FIG. 11 shows V-I characteristics of an organic transistor fabricated in comparative example 1.

FIG. 11 shows V-I characteristics. The on/off ratio has a low value of 3.6, and the mobility is $7.4 \times 10^{-4}$ $cm^2/Vs$. The threshold voltage Vth is difficult to control to a predetermined voltage, the average is −8V, and the variation is very large.

Comparative Example 2

The characteristics of an organic transistor obtained by forming an organic semiconductor layer 3 using a compound (5,5''''-di-n-hexyl-pentathiophene) (DH5T) is shown the following structure:

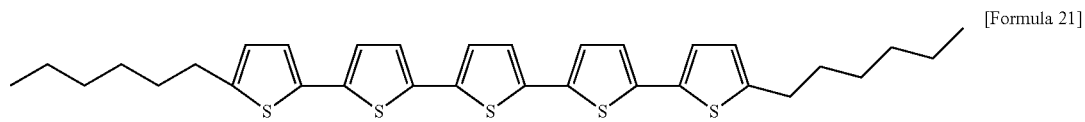

[Formula 21]

The channel length L is 0.05 mm and the channel width W is 1 mm.

Figure 12:
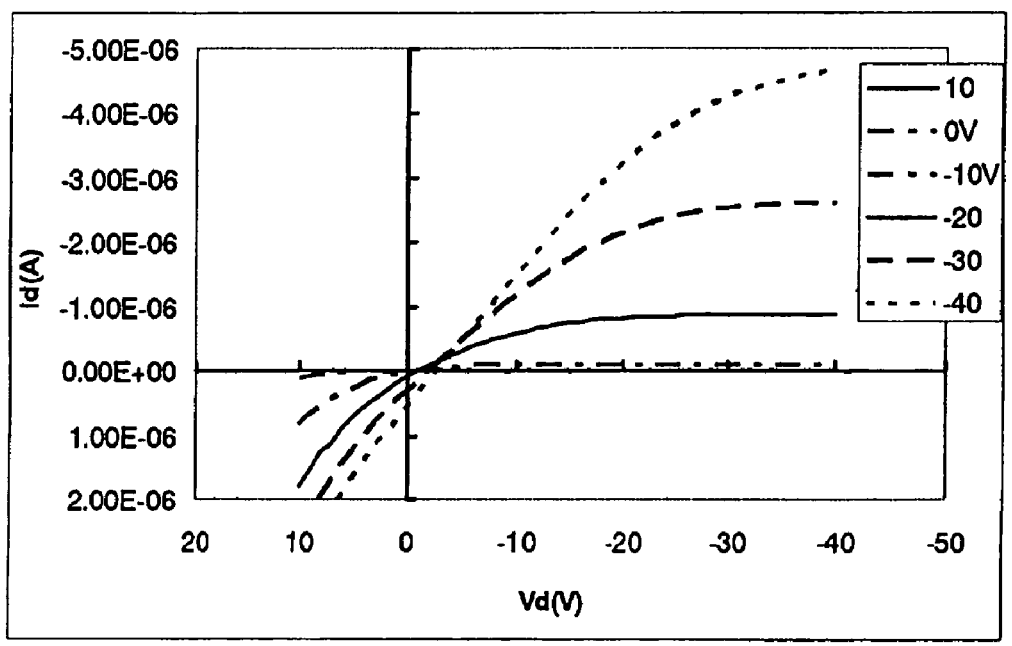
FIG. 12 shows V-I characteristics of an organic transistor fabricated in comparative example 2.

FIG. 12 shows the V-I characteristics. The on/off ratio is 4037, mobility is 0.0196 $cm^2/Vs$, and favorable transistor characteristics are obtained. The threshold voltage Vth, which is a voltage that the on state and the off state of the organic field effect transistor transits, is difficult to control to a predetermined voltage, the average is −0.14V, and the variation is very large.

As it is apparent from above, favorable transistor characteristics are obtained from the organic transistor, in which the organic semiconductor layer is formed by using the organic semiconductor material according to the present invention. Therefore, the organic semiconductor material according to the present invention has a high-carrier mobility and it provides favorable transistor characteristics when used in an organic transistor.

Embodiments 9 to 11

In order to compare a compound with a recurrence rate n at the oligothiophene part having an odd number and a compound having an even number, the compounds having even numbers have been synthesized according to the embodiments 9 to 11 below.

Synthesis of Embodiment 9

9,9-dioctyl-2,7-di(5''''-n-hexyl-tetrathiophene-2-yl) fluorene [Compound 9]

[Formula 22]

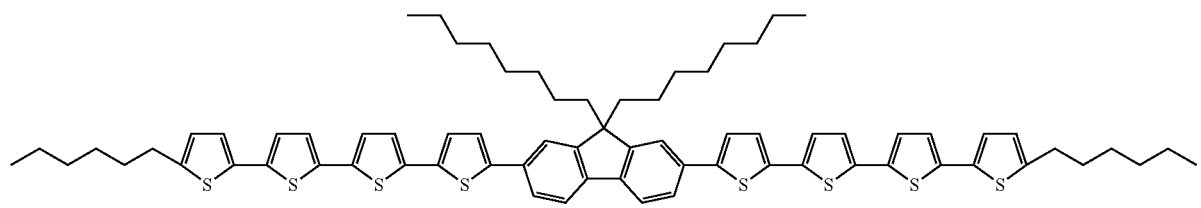

Add 9,9'-dioctyl-2,7-di(4,4,5,5-tetramethyl-1,3,2,-dioxaborolan-2-yl)fluorene (321 mg, 0.5 mmol), 5,5'-dibromo-2,2'-bithiophene (324 mg, 1 mmol), Suzuki coupling catalyst, 10 ml of toluene and 8 ml of a base solution for reaction. The temperature of the reaction chamber is increased to 95 degree/C. after repeating for three times a decompression-nitrogen substitution operation. The reaction is performed for approximately 4 hours at 95 degree/C. under a nitrogen atmosphere. Thereafter, add 5-(4,4,5,5-tetramethyl-1,3,2-dioxaborolan-2-yl)-5'-n-hexyl-2,2'-bithiophene (395 mg, 1.05 mmol) and further continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a yellow powder is obtained. The yield is 48%.

Synthesis of Embodiment 10

9,9-dioctyl-2,7-di(5''''-n-hexyl-tetrathiophene-2-yl) fluorene [Compound 10]

[Formula 23]

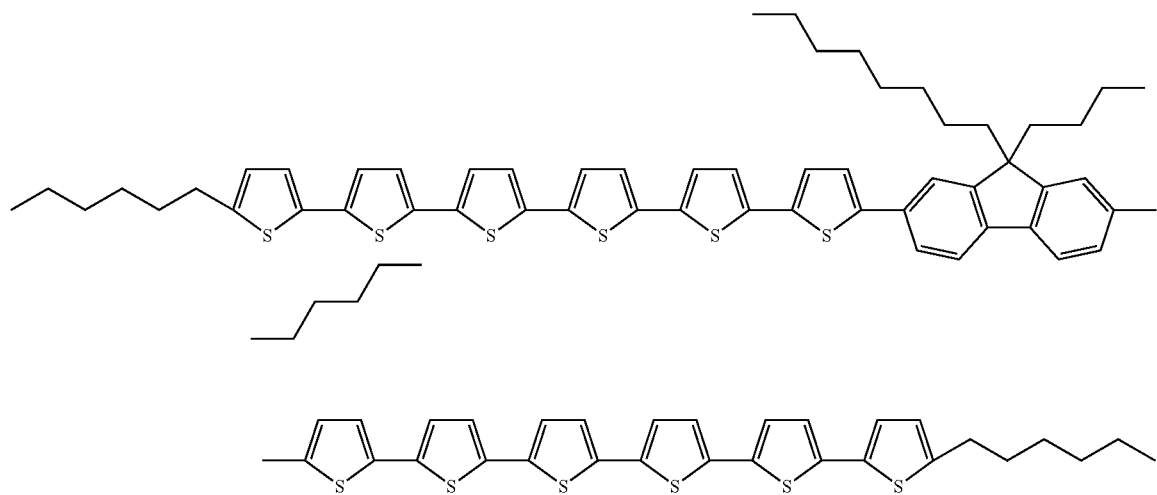

Add 2,5'-diiodethiophene (336 mg, 1 mmol), 5,5'-di(4,4,5,5-tetramethyl-1,3,2-dioxaborolan-2-yl)-2,2'-bithiophene (209 mg, 0.5 mmol), Suzuki coupling catalyst, 10 ml of toluene and 8 ml of a base solution for reaction. The temperature of the reaction chamber is increased to 95 degree/C. after repeating for three times a decompression-nitrogen substitution operation. The reaction is performed for approximately 4 hours at 95 degree/C. under a nitrogen atmosphere. Next, add 9,9-dioctyl-2,7-di(4,4,5,5-tetramethyl-1,3,2-dioxaborolan-2-yl)fluorene (160.5 mg, 0.25 mmol) and continue the reaction for three more hours at 95 degree/C. under a nitrogen atmosphere. Thereafter, add 5-(4,4,5,5-tetramethyl-1,3,2-dioxaborolan-2-yl)-5'-n-hexyl-2,2'-bithiophene (207 mg, 0.55 mmol) and further continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a yellow powder is obtained. The yield is 35%.

Synthesis of Embodiment 11

1,4-di(5'''-n-hexyl-tetrathiophene-2-yl)benzene [Compound 11]

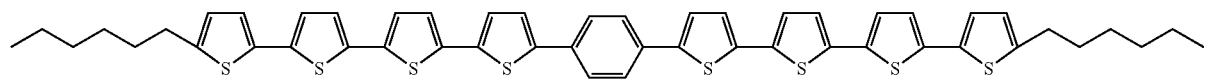

[Formula 24]

Add 5,5'-dibromo-bithiophene (162 mg, 0.5 mmol), 1,4-di(4,4,5,5-tetramethyl-1,3,2-dioxaborolan-2-yl)benzene (82.5 mg, 0.25 mmol), Suzuki coupling catalyst, 20 ml of anisole and 8 ml of a base solution for reaction. The temperature of the reaction chamber is increased to 95 degree/C. after repeating for three times a decompression-nitrogen substitution operation. The reaction is performed for approximately 4 hours at 95 degree/C. under a nitrogen atmosphere. Next, add 5-(4,4,5,5-tetramethyl-1,3,2-dioxaborolan-2-yl)-5'-n-hexyl-2,2'-bithiophene (207 mg, 0.55 mmol) and further continue the reaction for three more hours at 95 degree/C. under a nitrogen atmosphere.

After cooling the product, drop into 200 ml of methanol to precipitate the product. Next, wash this with methanol three times. After vacuum drying, dissolve the product in 100 ml of chloroform and purify with a column chromatography filled with silica gel using chloroform. After removing the solvent with a rotary evaporator and concentrating down to an adequate amount, drop into 200 ml of methanol to precipitate the product. Wash the precipitate three times with methanol, then vacuum dry. Ultimately, a yellow-brown powder is obtained. The yield is 17%.

[Fabrication of an Organic Transistor]

The organic transistors are fabricated as described above using compounds 9 to 11, and the characteristics are evaluated as described above. In any of the organic transistors, the channel length L is 0.05 mm and the channel width W is 1 mm. The results are shown in table 2. In table 2, the results for the compound 5, in which the recurrence rate n at the thiophene unit is 5, and the compound 6 in which the recurrence rate n at the thiophene unit is 3, are also shown.

Figure 13:
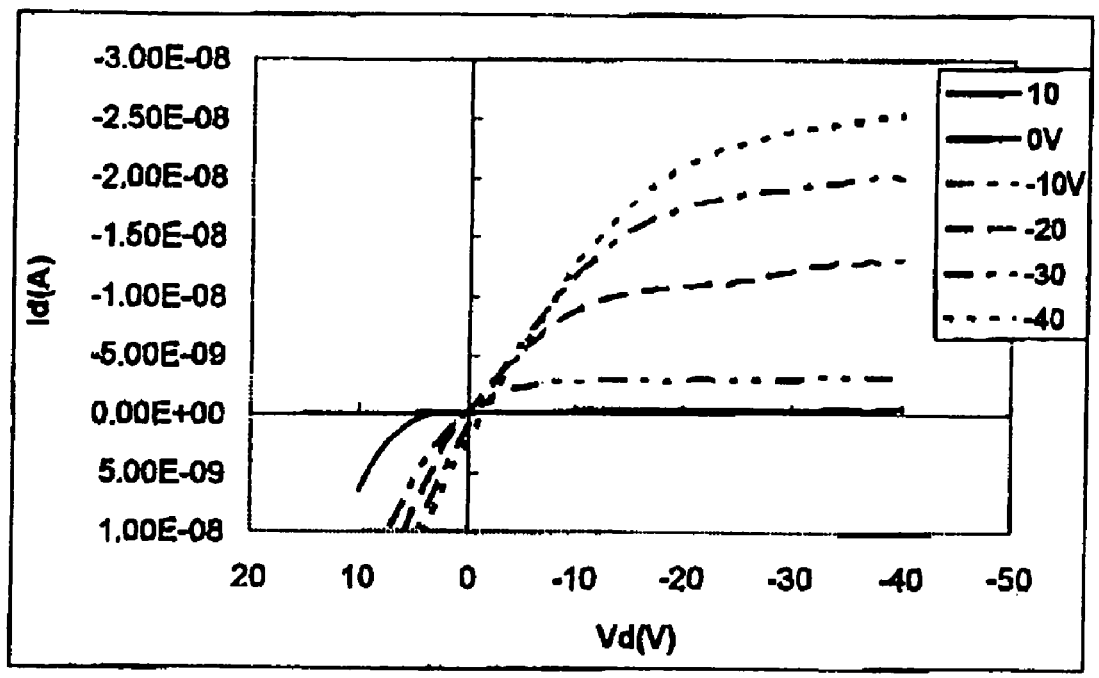
FIG. 13 shows V-I characteristics of an organic transistor fabricated in embodiment 9.
Figure 14:
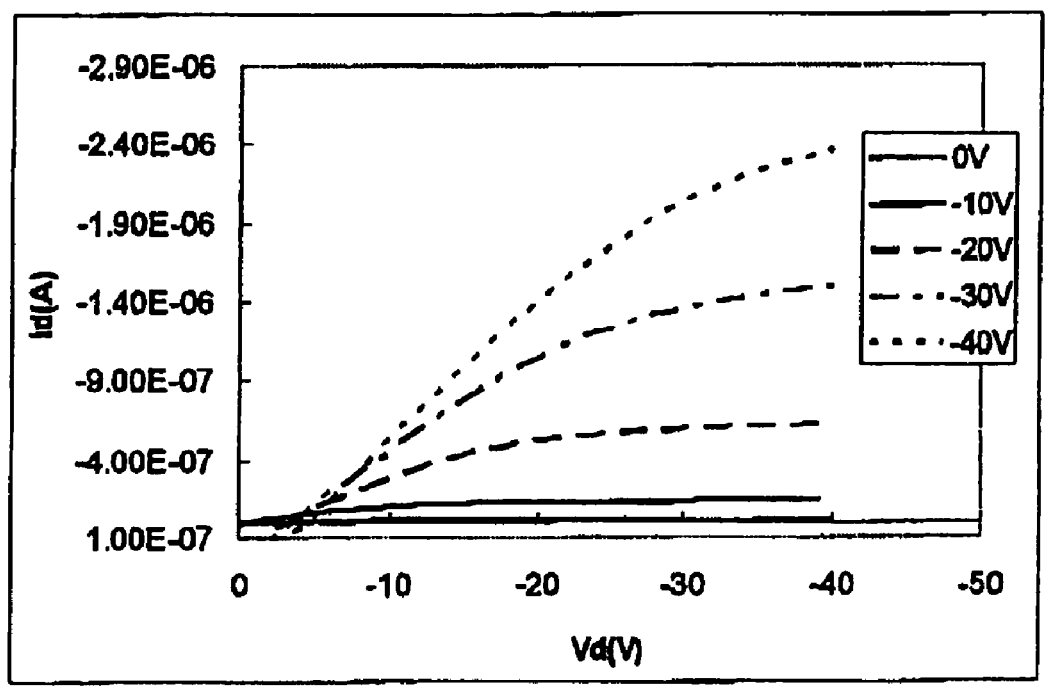
FIG. 14 shows V-I characteristics of an organic transistor fabricated in embodiment 10.
Figure 15:
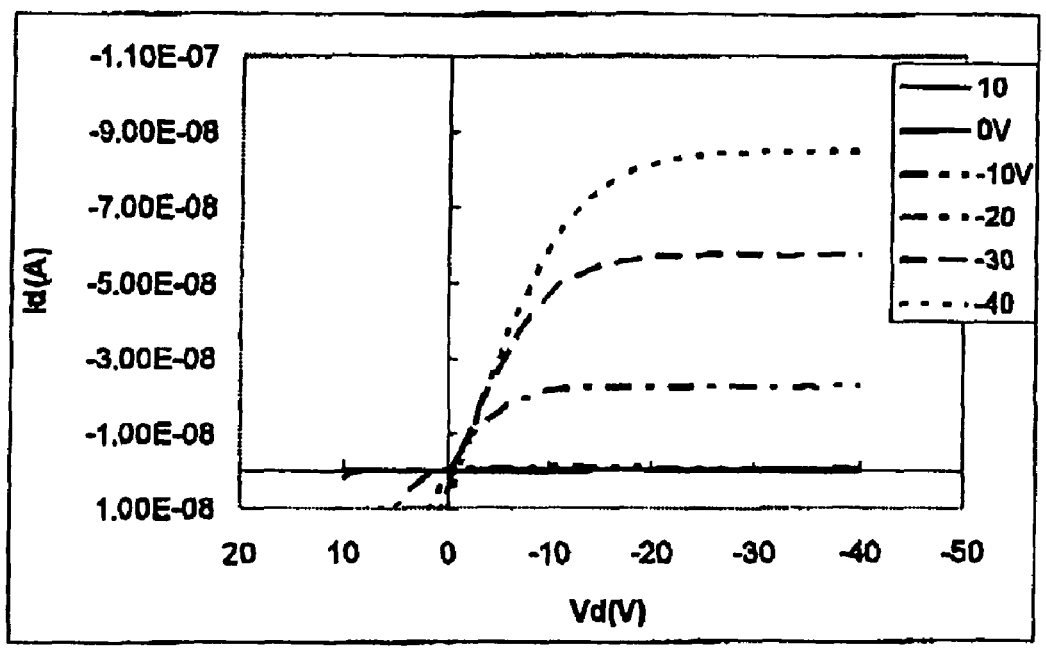
FIG. 15 shows V-I characteristics of an organic transistor fabricated in embodiment 11.

Further, FIG. 13 shows the V-I characteristics of the embodiment 9 (compound 9), FIG. 14 shows the V-I characteristics of the embodiment 10 (compound 10), and FIG. 15 shows the V-I characteristics of the embodiment 11 (compound 11).

TABLE 2

| Compound | Thiophene Unit Recurrence Rate n | On/Off Ratio | Mobility (cm²/Vs) | Threshold Voltage Vth (V) |
|---|---|---|---|---|
| Compound 9 | 4 | 62 | 0.000305 | −15.1 |
| Compound 5 | 5 | 39063 | 0.0422 | −8.84 |
| Compound 10 | 6 | 168 | 0.0073 | −5.58 |
| Compound 6 | 3 | 4160 | 0.185 | −3.12 |
| Compound 11 | 4 | 815 | 0.00103 | −9.89 |

As is apparent from the results shown in table 2, in the organic semiconductor material according the present invention, the on/off ratio and the mobility increases when the recurrence rate n at the thiophene unit is a odd number, and thereby favorable transistor characteristics can be obtained.

What is claimed is:

1. An organic semiconductor material comprising a following structure of an oligothiophene part and a connecting part G:

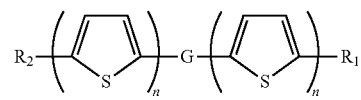

where, $R_1$ and $R_2$ are selected from a group consisting of: a hydrogen, an alkyl group, which is unsubstituted or substituted by one or more substitutents, an alkoxy group, which is unsubstituted or substituted by one or more substitutents, an aryl group, which is unsubstituted or substituted by one or more substitutents, or an alkenyl group, which is unsubstituted or substituted by one or more substitutents, or a combination of two or more thereof; and n is an integer;

wherein the connecting part G is selected from a group consisting of:

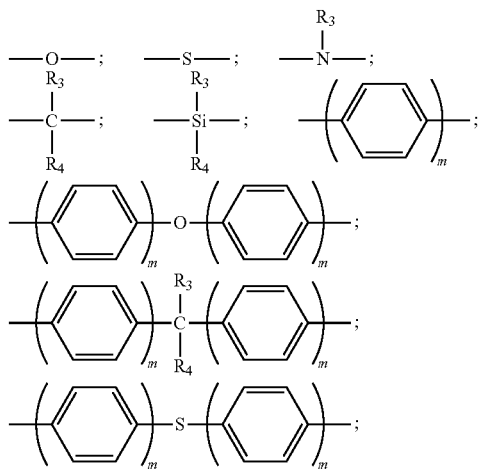

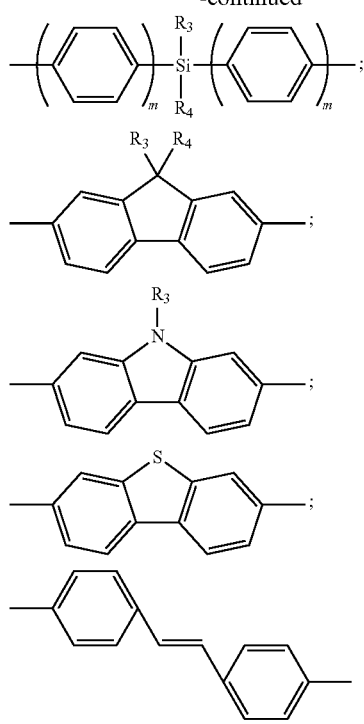

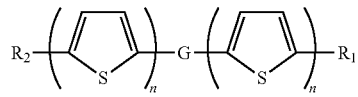

where, $R_1$ and $R_2$ are selected from a group consisting of: a hydrogen, an alkyl group, which is unsubstituted or substituted by one or more substitutents, an alkoxy group, which is unsubstituted or substituted by one or more substitutents, an aryl group, which is unsubstituted or substituted by one or more substitutents, or an alkenyl group, which is unsubstituted or substituted by one or more substitutents, or a combination of two or more thereof; and n is an integer;

wherein n comprises a number of repeat unit of thiophene, and where the number of repeat unit ranges from 3 to 11; and wherein the connecting part G is selected from a group consisting of:

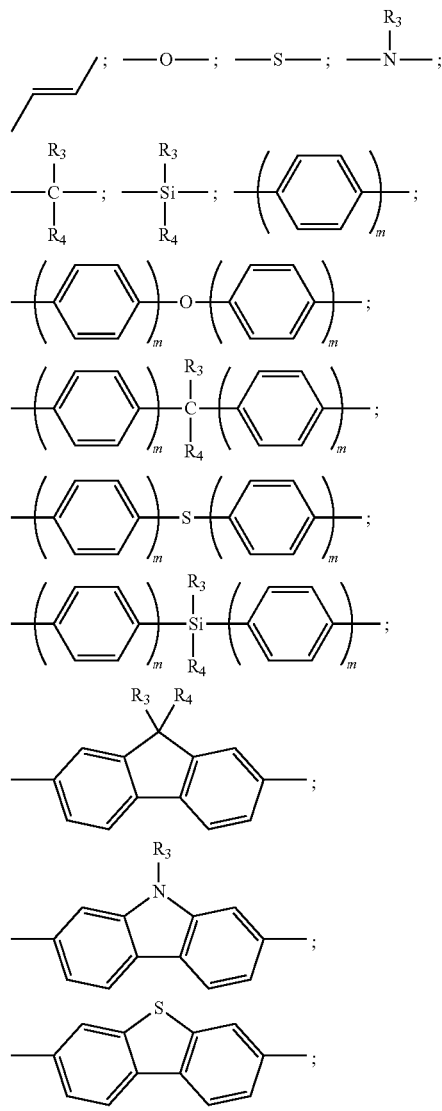

where, $R_3$ and $R_4$ are selected from a group consisting of: a hydrogen, an alkyl group, which is unsubstituted or substituted by one or more substitutents, an alkoxy group, which is unsubstituted or substituted by one or more substitutents, an aryl group, which is unsubstituted or substituted by one or more substitutents, or an alkenyl group, which is unsubstituted or substituted by one or more substitutents or a combination of two or more thereof; and m is an integer of 1 to 3;

wherein $R_1$ and $R_2$ are an alkyl group, which is unsubstituted or substituted by one or more substitutents, comprising four or more carbon numbers.

2. The organic semiconductor material according to claim 1, wherein n comprises a number of repeat unit of thiophene, and where the number of repeat unit ranges from 3 to 11.

3. The organic semiconductor material according to claim 1, wherein n comprises a number of repeat unit of thiophene, and where the number of repeat unit is selected from a group consisting of: 3, 5, 7, 9 or 11.

4. The organic semiconductor material according to claim 1, further comprising an organic transistor constructed of the organic semiconductor material.

5. A field effect transistor comprising a semiconducting layer and a gate electrode directly or indirectly contacting the semiconducting layer, where a current in the semiconducting layer is controlled by providing an electric field between the gate electrode and the semiconducting layer, wherein the semiconducting layer comprises an organic semiconductor material according to claim 1.

6. An organic semiconductor material comprising a following structure of an oligothiophene part and a connecting part G:

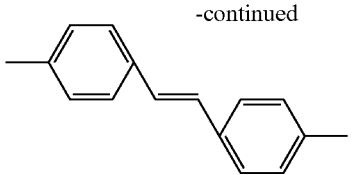

where, $R_3$ and $R_4$ are selected from a group consisting of: a hydrogen, an alkyl group, which is unsubstituted or substituted by one or more substitutents, an alkoxy group, which is unsubstituted or substituted by one or more substitutents, an aryl group, which is unsubstituted or substituted by one or more substitutents, or an alkenyl group, which is unsubstituted or substituted by one or more substitutents or a combination of two or more thereof; and m is an integer of 1 to 3.

7. The organic semiconductor material according to claim 6, wherein a molar mass of the connecting part G is approximately less than 5000.

8. The organic semiconductor material according to claim 6, wherein $R_1$ and $R_2$ are an alkyl group, which is unsubstituted or substituted by one or more substitutents, comprising four or more carbon numbers.

9. The organic semiconductor material according to claim 6, wherein n comprises a number of repeat unit of thiophene, and where the number of repeat unit is selected from a group consisting of: 3, 5, 7, 9 or 11.

10. The organic semiconductor material according to claim 6, further comprising an organic transistor constructed of the organic semiconductor material.

* * * * *